(12) United States Patent
Nakao et al.

(10) Patent No.: US 9,409,159 B2
(45) Date of Patent: Aug. 9, 2016

(54) SOLID PHOSPHORIC ACID CATALYST, AND METHOD FOR PRODUCING TRIOXANE

(71) Applicant: Clariant Catalysts (Japan) K.K., Tokyo (JP)

(72) Inventors: Hiroaki Nakao, Fuji (JP); Yutaka Kubota, Fuji (JP); Xin Chen, Toyama (JP)

(73) Assignee: CLARIANT CATALYSTS (JAPAN) K.K., Tokyo (JP)

( * ) Notice: Subject to any disclaimer, the term of this patent is extended or adjusted under 35 U.S.C. 154(b) by 0 days.

(21) Appl. No.: 14/890,870

(22) PCT Filed: Apr. 15, 2014

(86) PCT No.: PCT/JP2014/060743
§ 371 (c)(1),
(2) Date: Dec. 14, 2015

(87) PCT Pub. No.: WO2014/185205
PCT Pub. Date: Nov. 20, 2014

(65) Prior Publication Data
US 2016/0089661 A1    Mar. 31, 2016

(30) Foreign Application Priority Data

May 13, 2013 (JP) .................................. 2013-101541

(51) Int. Cl.
| | | |
|---|---|---|
| *B01J 27/182* | (2006.01) | |
| *C07D 323/06* | (2006.01) | |
| *B01J 37/08* | (2006.01) | |
| *B01J 21/12* | (2006.01) | |
| *B01J 21/16* | (2006.01) | |
| *B01J 27/16* | (2006.01) | |
| *B01J 35/02* | (2006.01) | |
| *B01J 35/10* | (2006.01) | |
| *B01J 37/02* | (2006.01) | |

(52) U.S. Cl.
CPC ................ *B01J 27/182* (2013.01); *B01J 21/12* (2013.01); *B01J 21/16* (2013.01); *B01J 27/16* (2013.01); *B01J 35/023* (2013.01); *B01J 35/1009* (2013.01); *B01J 35/1014* (2013.01); *B01J 37/0201* (2013.01); *B01J 37/082* (2013.01); *C07D 323/06* (2013.01)

(58) Field of Classification Search
CPC ...................................................... B01J 27/182
USPC .......................................................... 549/368
See application file for complete search history.

(56) References Cited

U.S. PATENT DOCUMENTS

| | | | |
|---|---|---|---|
| 5,508,448 | A | 4/1996 | Emig et al. |
| 6,124,480 | A | 9/2000 | Hoffmockel et al. |
| 6,313,323 | B1 | 11/2001 | Werner et al. |

FOREIGN PATENT DOCUMENTS

| | | |
|---|---|---|
| CA | 771679 A | 11/1967 |
| EP | 0714379 B1 | 10/1997 |
| JP | S44-12898 | 6/1965 |
| JP | S44-30735 | 12/1969 |
| JP | S59-25387 | 2/1984 |
| JP | S59-134789 | 8/1984 |
| JP | H7-2833 | 1/1995 |
| JP | 2001-11069 | 1/2001 |
| JP | 2005-230622 | 9/2005 |
| JP | 2014-024754 | 2/2014 |
| WO | WO2014/017203 | 1/2014 |

OTHER PUBLICATIONS

Busfield, et al.; "The Gas-phase Equilibrium between Trioxan and Formaldehyde: The Standard Enthalpy and Entropy of the Trimerisation of Formaldehyde" J. Chem. Soc. (A), 1969 pp. 2975-2977.
Suprun et al, Acidic catalysts for the dehydration of glycerol: Activity and deactivation, Journal of Molecular Catalysis A: Chemical, Elsevier, Amsterdam, NL, vol. 309, No. 1-2, Aug. 18, 2009, pp. 71-78.
Extended European search report in European Patent Application No. 14797038.8 dated May 25, 2016.

*Primary Examiner* — Taofiq A Solola
(74) *Attorney, Agent, or Firm* — Knobbe Martens Olson & Bear LLP (57) ABSTRACT

A solid phosphoric acid catalyst which, when gas-phase synthesizing trioxane from formaldehyde, results in production of trioxane at a high yield and at a high selection rate by markedly suppressing side reactions, reduces the adhesion of organic matter to the catalyst surface, and achieves a stable and long-term catalyst reaction. This solid phosphoric acid catalyst contains silicon phosphate oxide (SPO) obtained by sintering at a temperature of at least 200° C. a carrier material to which a phosphoric acid component has been added, and the total quantity of acid does not exceed 5 mmol per 1 g of solid phosphoric acid catalyst when calculated as acid quantity determined by $NH_3$-TPD measurement.

8 Claims, 1 Drawing Sheet

SOLID PHOSPHORIC ACID CATALYST, AND METHOD FOR PRODUCING TRIOXANE

TECHNICAL FIELD

The present invention relates to a solid phosphoric acid catalyst, and to a method for producing trioxane.

BACKGROUND ART

Trioxane, which is an annular trimer of formaldehyde, is a raw material monomer which is widely used in the production of polyoxymethylene (POM), and production methods thereof have long been established. For example, a method comprising a step of generating trioxane by the action of a non-volatile acid represented by sulfuric acid, phosphoric acid or the like in a liquid phase on a concentrated formaldehyde aqueous solution, a step of boiling this trioxane along with water including formaldehyde, and a step of purifying the above trioxane by extraction with an organic solution or recrystallization is known. However, the reaction equilibrium concentration in the liquid phase is extremely low. Thus, vaporization of the reaction product from the reaction system in order to increase the equilibrium concentration of the trioxane is practiced, but the vaporization of the reaction product containing water is generally accompanied by a very high energy consumption.

Thus, a method of synthesizing trioxane by trimerizing directly in the gas phase from formaldehyde gas has long been studied. As mentioned in the research examples of Non-Patent Document 1, because the equilibrium concentration in the gas phase is higher than the equilibrium concentration in the liquid phase, it is expected that the synthesis of trioxane in the gas phase will provide a higher yield of trioxane than synthesis in the liquid phase, and it is also expected to reduce energy consumption in the manufacturing process.

As an example of trimerization directly in the gas phase from formaldehyde, in Patent Documents 1 to 4, upon reacting formaldehyde gas in the gas phase, as the supply source of the formaldehyde gas which is the raw material thereof, methods of pyrolysis of paraformaldehyde, and α-polyoxymethylene, or vaporization of a formaldehyde aqueous solution are mentioned. However, because water is present in the raw materials at a level of several % to several tens of %, this is no only disadvantageous with respect to the gas phase reaction, but there are also the problems that deactivation of the catalyst by large amounts of water, or repolymerization of the formaldehyde gas which is the raw material (paraform conversion), and the like, may readily occur.

Further, as the catalyst used for trioxane gas phase synthesis, the use of solid support bodies of various metal oxides, sulfides, and halides, or metal sulfates, phosphates, organic sulfonates and the like, and further, a support body of a silica gel or the like of a heteropoly acids, and solid acid catalysts of sulfonate type cation exchanged resins or the like, have been proposed (for example, refer to Cited Publications 1 to 4). However, there are the problems that metal oxides or sulfides, halides, or various metal salts may generate basic points or the like due to the presence of impurities deriving from other metal components, and side reactions are readily induced, and a satisfactory yield or selectivity of the trioxane will not necessarily be obtained. Further, due to the problem that heteropoly acids themselves are readily reduced, a strong acid strength and the like, deterioration of the catalyst or coking phenomena due to adhesion of organic matter may readily occur, and discoloration of the catalyst itself after the reaction can be notable. Further, solid acid catalysts represented by cation exchanged resins are useful, but also have shortcomings such as generally having low heat resistance.

As other catalysts, the use of vanadyl hydrogenphosphate semihydrate has also been proposed (Patent Document 5). However, for vanadyl hydrogenphosphate semihydrate, in consideration of the trioxane gas phase equilibrium concentration disclosed in Non-Patent Document 1, a satisfactory value for the trioxane yield has not been achieved.

Further, a method of trimerizing by a heterogeneous system catalyst gas phase reaction of gaseous formaldehyde having a low moisture content using a solid phosphoric acid catalyst comprising silicon phosphate, boron phosphate, aluminum phosphate, zirconium phosphate, titanium phosphate, zinc phosphate, or phosphate salt mixtures, or mixed compounds thereof has also been proposed (Patent Document 6). This method is advantageous in the point that a value close to the gas phase equilibrium concentration can be obtained, but considering the reaction selectivity to trioxane, it does not necessarily provide a satisfactory result. Further, there are problems such as deposition of carbon substances due to polymerization of formaldehyde (paraform conversion) on the surface of the phosphoric acid catalyst, and the like, and in the point of the long term reaction stability•catalyst life, there is demand to further enhance solid phosphoric acid catalysts.

Patent Document 1: Japanese Examined Patent Application Publication No. S40-12898
Patent Document 2: Japanese Examined Patent Application Publication No. S44-30735
Patent Document 3: Japanese Unexamined Patent Application, Publication No. S59-25387
Patent Document 4: Japanese Unexamined Patent Application, Publication No. S59-134789
Patent Document 5: Japanese Unexamined Patent Application, Publication No. H07-2833
Patent Document 6: Japanese Unexamined Patent Application, Publication No. 2001-11069
Non-Patent Document 1: W. K. Busfield et al., J. Chem. Sci (A) 1969, 2975

DISCLOSURE OF THE INVENTION

Problems to be Solved by the Invention

As described above, so far many methods of synthesizing trioxane in the gas phase from formaldehyde gas have been disclosed, and at the same time, many solid acid catalysts relating to gas phase synthesis have also been exemplified. However, almost no specific examples have been shown which can provide a high reaction conversion ratio (yield) corresponding to the gas phase equilibrium concentration of trioxane, while at the same time notably suppressing secondary products such as methanol, methyl formate, methylal and the like. Moreover, there is the problem that in the prior art catalysts, discoloration or activity degradation or the like of the catalyst due to deposition of carbon substances (coking) due to adhesion of organic matter or the like at the catalyst surface, oxidation•reduction or the like, are frequently observed. Accordingly, in the synthesis of trioxane in the gas phase from formaldehyde gas, there is demand for a solid acid catalyst which can be used stably and with long life, and for establishing a production method of trioxane using this catalyst.

The present invention is one which was made with the objective of solving the above problems, and is one which creates a catalyst system which can notably suppress discoloration, degradation, and lifespan reduction of the catalyst itself, along with efficiently promoting the gas phase equilibrium reaction from formaldehyde gas to trioxane, by suppressing side reactions to a higher degree than the prior art. A catalyst used for this objective has a controlled acid quantity and structure, and is able to provide a stable and long term production process in the gas phase synthesis of trioxane. Further, the present catalyst is not limited to the above described trioxane gas phase synthesis, but it can also be widely applied to various reactions where solid acid catalysts are generally used, for example, esterification, alkylation, partial oxidation, hydration reactions, dehydration, isomerization or dimerization, and polymerization reactions and the like.

Means for Solving the Problems

The present inventors carried out repeated diligent research focusing on the type and acid quantity of solid acid catalysts, and preparation methods of solid acid catalysts, for the synthesis of trioxane in the gas phase from a formaldehyde aqueous solution. As a result, it was discovered that by limiting the type of phosphorous compound in the solid phosphoric acid catalyst, and further restricting the acid quantity to be no more than a defined level, along with setting to a high temperature the sintering temperature when preparing the solid acid catalyst, by controlling the structure such that the average specific surface area of the catalyst is no more than a fixed value, it is possible to not only bestow a high yield•high selectivity with respect to trioxane gas phase synthesis, but also to realize a stable and long term catalytic reaction by reducing the adhesion of organic matter and the like, and the deposition of carbon substances on the catalyst surface, whereby the present invention was completed. More specifically, the present invention provides the following.

(1) The present invention is a solid phosphoric acid catalyst comprising a silicon phosphate oxide, wherein a quantity of acid determined by an $NH_3$-TPD measurement method is no more than 5 mmol per 1 g of catalyst mass.

(2) Or, the present invention is a solid phosphoric acid catalyst according to (1), wherein a specific surface area according to a BET method is no more than 20 $m^2/g$.

(3) Or, the present invention is a solid phosphoric acid catalyst according to (1) or (2), wherein a carrier is one or more selected from porous silica, aluminum hydrosilicate, or diatomaceous earth.

(4) Or, the present invention is a solid phosphoric acid catalyst according to (3), wherein the silicon phosphate oxide is a dehydrated composite compound of the carrier, and one or more phosphoric acid selected from orthophosphoric acid, pyrophosphoric acid, or polyphosphoric acid, or a precursor of these phosphoric acids.

(5) Or, the present invention is a solid phosphoric acid catalyst according to any one of (1) to (4), obtained by sintering a carrier material to which a phosphoric acid component is attached at no less than 200° C.

(6) Or, the present invention is a method for producing trioxane wherein the solid phosphoric acid catalyst according to any one of (1) to (5) is charged into a reaction vessel, and formaldehyde gas and the solid phosphoric acid catalyst are contacted in a heterogeneous system, whereby trioxane remaining in a gas phase state is continuously extracted from the reaction vessel.

(7) Or, the present invention is a method for producing trioxane according to (6), wherein the reaction vessel is a cylindrically shaped fixed bed reaction vessel with an inner diameter of no more than 100 mm, and the solid phosphoric acid catalyst having an average particle diameter of no more than 10 mm is charged into the fixed bed reaction vessel.

(8) Or, the present invention is a method for producing trioxane according to (6) or (7), wherein, in the reaction vessel in which the solid phosphoric acid catalyst is charged a temperature measurement means which measures a temperature of a reaction product gas at a catalyst bet exit, and a control means which controls a temperature of a heating medium and/or a flow rate of the formaldehyde gas such that a temperature measured by the temperature measurement means is within a range of 80° C. to 120° C., are provided.

Effects of the Invention

In the solid phosphoric acid catalyst produced according to the conditions disclosed in the present invention, the composition components are controlled, and the acid quantity and catalyst surface area are limited to no more than defined levels, and therefore, the reaction can be carried out quickly without the formaldehyde gas, which is the reaction substrate, being unnecessarily retained inside the catalyst (for example, inside the pores), and it is possible to greatly restrict side reactions with respect to the gas phase synthesis of trioxane, and further it is possible to effectively restrict discoloration of the catalyst or deposition of carbon substances even with respect to the contamination of organic matter or the like other than formaldehyde in the reaction gas. A solid phosphoric acid catalyst having its structure controlled in this way is able to realize a high yield•selectivity for trioxane gas phase synthesis from formaldehyde gas.

PREFERRED MODE FOR CARRYING OUT THE INVENTION

The present invention is one which relates to a solid phosphoric acid catalyst and to a method for producing trioxane using this catalyst, and is one which discloses a solid phosphoric acid catalyst where the composition•acid quantity of the used catalyst, and further the specific surface area of the catalyst, are controlled to be no more than fixed values. The use of this solid phosphoric acid catalyst in the gas phase synthesis of trioxane shows superiority in the following points.

(1) A high conversion rate of trioxane from formaldehyde (high yield).

(2) A high selectivity towards a trioxane reaction (low side reactions).

(3) Suppression of the carbonization phenomena (coking) accompanying the suppression of adhesion of organic matter and the like on the catalyst, and extended life of the catalyst.

Below, specific examples of the present invention are explained in detail, but the present invention is not in any way limited to these examples, and may be implemented with the addition of suitable modifications within the scope of the objective of the present invention.

Solid Phosphoric Acid Catalyst

The solid phosphoric acid catalyst of the present invention comprises a silicon phosphate oxide, and is a solid phosphoric acid catalyst with a quantity of acid determined by the $NH_3$-TPD measurement method of no more than 5 mmol per 1 g of the catalyst mass. This solid phosphoric acid catalyst may be obtained, for example, by precipitating a phosphoric acid and an elemental salt including components of the carrier, or adding a phosphoric acid to the carrier material, and further subjecting these to a sintering treatment at a temperature of no less than 200° C.

The silicon phosphate oxide is stable because it is compounded by the dehydration of the silicic acid of the carrier and phosphoric acid, has a high reaction conversion rate to trioxane, and is also favorable with respect to discoloration or coking of the catalyst itself. On the other hand, the case where the acid is only a separate phosphoric acid is not preferable in that not only does the phosphoric acid readily detach from the catalyst, but the activity•selectivity towards the trioxane reaction also tends to be degraded.

The silicon phosphate oxide of the present catalyst can be confirmed by the X-ray diffraction method (XRD). This silicon phosphate oxide is one where, among the carrier components, a chemical bond is formed for example by dehydration of a hydroxyl group of a silicic acid derivative and the phosphoric acid, and therefore, it has a crystal structure as a composite oxide, whereby it is possible to detect an XRD pattern. On the other hand, an separate phosphoric acid (for example, a component not having a chemical bond to the carrier, such as orthophosphoric acid or pyrophosphoric acid or the like) has low crystallinity, or has no crystallinity, and therefore, is difficult to detect by usual XRD.

The solid phosphoric acid catalyst of the present invention is sintered at a temperature of no less than 200° C., and it is thought that at this time, the silicon phosphate oxide is formed by chemical bonding of the phosphoric acid and the carrier. In the present invention, it is a requirement that this silicon phosphate oxide is present at the catalyst.

Further, the acid quantity in the catalyst can be determined by the $NH_3$-TPD measurement method. The $NH_3$-TPD measurement method refers to a thermal desorption method using an ammonia component as an adsorbed molecule, and is a non-equilibrium technique wherein, as the temperature of a catalyst sample is continuously increased, the progress of the desorption of the ammonia adsorbed molecule is measured, whereby the acid quantity on the catalyst is evaluated.

The catalyst according to the present invention is required to include a silicon phosphate oxide. Moreover, in this case, the acid quantity according to the $NH_3$-TPD method is required to be no more than 5 mmol per 1 g of the catalyst. If 5 mmol is exceeded, not only are side reactions other than trioxane readily induced, but also, the formaldehyde itself which is the reaction matrix, and trace amounts of other organic compound components will readily be adsorbed in large quantities on the catalyst, to become a primary cause of coking such as deposition of carbon substances and the like, and this is not preferable.

The size of the average specific surface area of the solid phosphoric acid catalyst is not particularly limited, but in order to prevent the occurrence of side reactions, along with preventing discoloration of the catalyst attributed to the deposition or the like of carbon substances by excessive contact with the reaction matrix or trace amounts of other organic compound components, and to prevent the induction of coking, it is preferably no more than 20 $m^2/g$. Further, in the present specification, the average specific surface area refers to the average surface area per unit catalyst mass according to the BET method.

The carrier of the solid phosphoric acid catalyst is not particularly limited, but in order to prevent inducing side reactions due to basic points included in the carrier, it is preferably porous silica, aluminum hydrosilicate or diatomaceous earths, more specifically, one of, or mixtures of two or more of porous silica, silica-alumina, aluminum hydrosilicate or natural silica such as diatomaceous earths or attagel, or natural silicates. If the carrier is another carrier, for example, only alumina, titania, or a zeolite or the like, compared to the case that it is porous silica, aluminum hydrosilicate or diatomaceous earths, side reactions can be induced by the basic points included in the carrier.

The above silicon phosphate oxide is not particularly limited provided that it is a dehydrated composite compound of the carrier and a phosphoric acid or a phosphoric acid precursor, but from the viewpoint of easily manifesting a stable acidity as the solid acid, the above phosphoric acid is preferably one or more selected from orthophosphoric acid, pyrophosphoric acid, and polyphosphoric acid. In the present Examples, a phosphoric acid precursor refers to one which becomes a phosphoric acid by hydrolysis, for example, a phosphate ester or the like may be mentioned.

Concerning the form of the solid phosphoric acid catalyst, it is not particularly limited to a powder form, granular form, pellet form by molding, or the like, but usually, in the case of carrying out trioxane gas phase synthesis with an fixed bed reactor, in consideration of the problem of pressure loss in the catalyst bed and the like, a molded body is preferable. There are no particular restrictions concerning the form of the molded body, and for example, it may be various types of molded body such as pellet form, plate form, granular form, and the like, prepared by a method of extrusion molding, tablet molding, spray drying, tumbling granulation, granulation in oil, and the like. Further, the particle diameter of these molded bodies is not particularly limited, but in consideration of a uniformly charged state of the catalyst in the fixed bed reactor, and effective contact with the reaction gas and the like, 10 mm or less, and preferably, a range on the order of 0.5 to 6 mm can be suitably used.

Method for Producing the Solid Phosphoric Acid Catalyst

Next, the method for producing the solid phosphoric acid catalyst in the present invention will be explained.

As described above, as the solid phosphoric acid catalyst in the present invention, one where an elemental salt comprising components of the phosphoric acid and the carrier is precipitated, or one where the phosphoric acid is attached to the carrier material, can be mentioned. Namely, as the preparation method thereof, a coprecipitation method or an impregnation method can be mentioned. Among these, as a impregnation method, there are a method of directly spraying an aqueous solution of the phosphoric acid onto the carrier, and a method of kneading the carrier and the phosphoric acid aqueous solution.

One example of the preparation method of the solid phosphoric acid catalyst used in the present invention is shown below, but it is not limited to this method or these steps. First, an aluminum hydrosilicate which is spherical particles having an average particle diameter of 5.4 mm (made by Clariant Catalysts K.K.) was readied as the carrier, and to this, orthophosphoric acid (for example, reagent grade; made by Wako Pure Chemical Industries, Ltd.) is sprayed and impregnated under a vacuum at 80° C. such that the phosphoric acid supported amount becomes a predetermined amount (ultimately, no more than 5 mmol/g as an acid quantity according to the $NH_3$-TPD measurement), whereby the catalyst precursor was prepared. After this, the present catalyst can be prepared by sintering the catalyst precursor for 2 hours at no less than 200° C. under an air atmosphere. By sintering at a temperature of no less than 200° C., a dehydration reaction resulting from the moisture or hydroxyl groups in the phosphoric acid and the carrier occurs, whereby a silicon phosphate oxide can be formed. Further, in addition to being able to impart sufficient strength with respect to the solid phosphoric acid catalyst, it is also possible to provide a uniform pore volume and specific surface area.

Applied Use of the Solid Phosphoric Acid Catalyst

The solid phosphoric acid catalyst used in the present invention may be suitably used in a gas phase reaction of formaldehyde gas to trioxane, but is not limited to this. Generally, besides being used as the solid acid catalyst in applications of various widely known organic synthesis reactions, for example, esterification, etherification, alkylation, hydration reactions, partial oxidation reactions, hydrolysis reactions, dehydration, isomerization, dimerization, polymerization reactions and the like, it may also be applied to the field of environmental catalysts such as desulfurization catalysts and the like. To mention only a very small proportion of examples, there are alkylation reactions of aromatic hydrocarbons by aliphatic hydrocarbons as represented by cumene synthesis, alcohol synthesis by hydration reactions of various olefins starting with ethylene, dimerization or polymerization reactions of olefins, partial oxidation reactions of aliphatic hydrocarbons such as n-butane and the like, but generally, there are manifold applications for the solid phosphoric acid catalyst, which are not limited to these examples.

Production Method of Trioxane

Next, referring to FIG. 1, a preparation method of trioxane in the present invention will be explained.

[Trioxane Preparation Apparatus 1]

Figure 1:
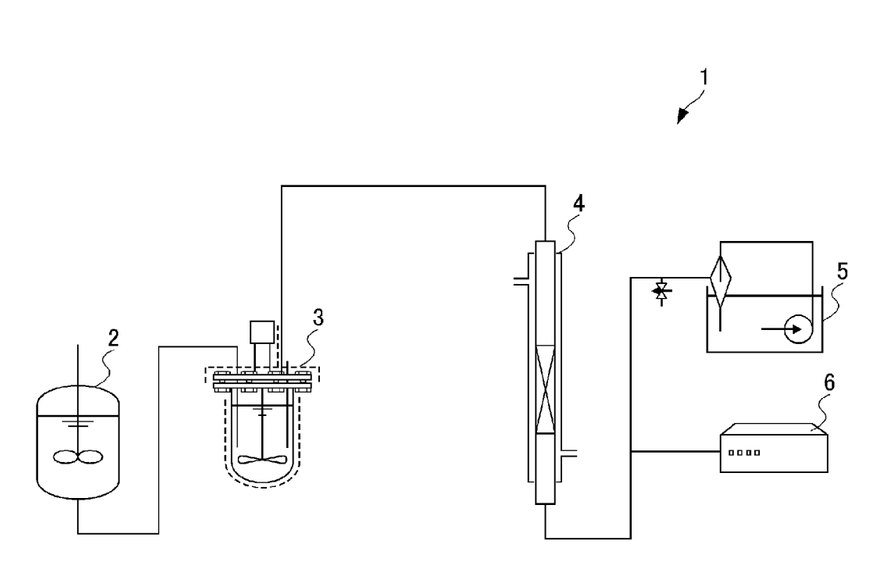
FIG. 1 is a FIGURE schematically showing one example of an apparatus arrangement for preparing a hemiformal from an aqueous solution of formaldehyde and an alcohol, and further carrying out gas phase trioxane synthesis from formaldehyde gas generation.

FIG. 1 is a schematic diagram showing a trioxane preparation apparatus 1 according to the present invention. The trioxane preparation apparatus 1 is provided with a hemiformal generation apparatus 2 which generates a hemiformal from a formaldehyde aqueous solution (formalin) and an alcohol, a hemiformal pyrolysis vessel 3 which pyrolyzes the hemiformal, a reaction vessel 4 wherein the above solid phosphoric acid catalyst is charged, and the above formaldehyde gas and the solid phosphoric acid catalyst are contacted in a heterogenous system, whereby a reaction product gas including trioxane and unreacted formaldehyde gas is produced remaining in the gas phase, an absorption apparatus 5 where trioxane from the above reaction product gas is absorbed in a solvent, and an analysis apparatus 6 for analyzing the components of the reaction product gas. [Hemiformal Generation Apparatus 2]

In the hemiformal generation apparatus 2, by making the formaldehyde aqueous solution and the alcohol react•dehydrate, a hemiformal concentrate is generated. First, the formaldehyde aqueous solution and alcohol are mixed, and a hemiformal aqueous solution is obtained. Then, this hemiformal aqueous solution is concentrated by dehydration and a low moisture content hemiformal concentrate is obtained. In this way, the hemiformal concentrate is generated.

Incidentally, formaldehyde gas is an essential raw material for trioxane gas phase synthesis, and as is clear from prior art patent documents, a generation method by vaporizing a concentrated formaldehyde aqueous solution, pyrolysis of paraformaldehyde or α-polyoxymethylene are representative. Further, directly obtaining an anhydrous formaldehyde gas by a nonoxidative method from methanol (dehydrogenation method) is also possible. However, in the present Examples, it is desirable to adopt a hemiformal, and to obtain a formaldehyde gas by a pyrolysis reaction from a hemiformal. By adopting a hemiformal, it becomes possible to prepare a formaldehyde gas with a low moisture content in the later steps because it is possible to effectively eliminate moisture from inside the system beforehand, which is advantageous in the points of the reaction yield, and selectivity and catalyst life in the trioxane gas phase synthesis.

The mixing conditions of the (A) formaldehyde aqueous solution and the (B) alcohol are not particularly limited, and the same reaction conditions of the formaldehyde aqueous solution and the alcohol as in well-known prior hemiformal conversion methods may be adopted. For example, the reaction temperature is preferably from room temperature (about 20° C.) to 90° C. Further, concerning the reaction time, this may be suitably set in accordance with the state of progress of the reaction or the like. Further, the mixing ratio of the two is not particularly limited, but a mole ratio of the hydroxyl groups in the (B) alcohol with respect to the (A) formaldehyde aqueous solution is preferably 0.3 to 5.0, and more preferably 0.5 to 2.0. If there is too little alcohol (no more than 0.3), there will be too much separate formaldehyde in the hemiformal aqueous solution, which is not preferable because when later carrying out the pressure reduction•dehydration reaction, the loss of the formaldehyde becomes high. Further, in the case that there is too much alcohol (no less than 5.0), when pyrolyzing the hemiformal in the hemiformal pyrolysis vessel 3, a need arises to supply large quantities of the hemiformal in order to produce a fixed amount of the formaldehyde gas, and this is not preferable because it becomes a disadvantage from the viewpoint of the energy required for pyrolysis.

The type of alcohol used in the preparation of the hemiformal aqueous solution is not particularly limited, but is desirably one selected from mono, di, or triols having a boiling point of no less than 190° C., or combinations thereof. In the case that the boiling point of the alcohol is lower than 190° C., when dehydrating•concentrating the hemiformal aqueous solution, the loss due to the volatization of the alcohol itself become large, and a recovery operation becomes necessary, which is not preferable. Further, the alcohol is volatilized when the hemiformal is pyrolyzed in the hemiformal pyrolysis vessel 3, therefore, this is also not preferable in the point that a need arises for providing a cooling vessel with the objective of recovering the alcohol.

As examples of alcohols with a boiling point of no less than 190° C., methylpentanediol, hexanetriol, pentanediol, methylbutanediol and the like can be mentioned as hydrophilic alcohols. In particular, 3-methyl-1,5-pentanediol, 1,2,6-hexanetriol, 1,5-pentanediol, or 3-methyl-1,3-butanediol and the like can be suitably used. Further, diethylpentanediol, ethylhexanediol, octanol, and the like can be mentioned as hydrophobic alcohols. In particular, as the diethylpentanediol, 2,4-diethyl-1,5-pentanediol, 2,3-diethyl-1,5-pentanediol, 1,4-diethyl-1,5-pentanediol, 1,5-diethyl-1,5-pentanediol, and the like can be mentioned as examples. Further, as the ethylhexanediol, 2-ethyl-1,3-hexanediol, 3-ethyl-1,3-hexanediol, 4-ethyl-1,3-hexanediol, and the like can be mentioned as examples.

Further, besides the above, it is also possible to adopt alkyleneglycols, polyalkyleneglycols and the like which are used in well known techniques for the preparation of hemiformals. As alkyleneglycols, there are diethylene glycol, triethylene glycol, tetraethylene glycol, and the like, and as the polyalkyleneglycol, there are polyalkyleneglycols with 5 or more ethylene oxide units, and further, polypropylene glycol, polytetramethylene glycol, and the like. Further, it is also possible to use derivatives and the like of polyalkyleneglycols. As derivatives of polyalkyleneglycols, there are block copolymers consisting of oxyethylene and oxypropylene, oxytetraethylene and the like, or polyalkylene glycols prepared as chain transfer agents of polyvalent alcohols and the like, and the like.

Such alcohols can be produced by using common methods. Further, commercially purchased ones may also be used.

The conditions for concentrating the hemiformal aqueous solution by dehydration and obtaining a low moisture content hemiformal concentrate are not particularly limited, but it is preferable to suitably set the temperature and pressure as the conditions at the time of the above dehydration•concentration, in consideration of the residual moisture content included in the hemiformal concentrate. Specifically, it is preferable to select a temperature in the range of 50° C. to 80° C., and it is preferable to select a pressure of no more than 50 mmHg.

The hemiformal concentrate after concentration still contains minute amounts of water, but due to the dehydration•concentration operation conditions it is generally no more than 1.0 mass %.

The concentration of the formaldehyde aqueous solution used in the preparation of the hemiformal concentrate is not particularly limited, but is preferably from 1 mass % to 80 mass % formaldehyde.

[Hemiformal Pyrolysis Vessel 3]

In the hemiformal pyrolysis vessel 3, the step of generating a formaldehyde gas by pyrolyzing the hemiformal concentrate is carried out. By this step, a highly pure formaldehyde gas can be obtained, but the method thereof is a general, well known technique. The temperature conditions of the pyrolysis are held at a high temperature (usually no less than 140° C.) so that it is possible to sever the hemiformal bond, but it is possible to suitably adjust this in combination with the operating pressure in the hemiformal pyrolysis vessel 3. Generally, a range of 140 to 180° C. is appropriate, and if the temperature is too low, the decomposition rate cannot be increased, and on the other hand, if too high, the problem occurs of the alcohol constituting the hemiformal volatilizing•degenerating and the like, which is not preferable. The hemiformal pyrolysis vessel 3 is not particularly limited, and it is possible to use various pyrolysis apparatuses, evaporators with various tank forms, cylindrical forms, columnar forms, or the like, implemented in batch form, semi-batch form, and continuous form.

The formaldehyde gas generated by the hemiformal pyrolysis can be handled as-is as a raw material of the gas phase synthesis of trioxane, but in order to further reduce the remaining moisture, and prevent contamination of the reaction vessel 4 by volatilized alcohol, a cooling vessel (condenser, not shown in the FIGURE) can be installed at the exit side of the hemiformal pyrolysis vessel 3, and by condensing the remaining moisture and volatilized alcohol component, the formaldehyde gas can be further purified.

[Reaction Vessel 4]

The above solid phosphoric acid catalyst is charged into the reaction vessel 4, and by making the above formaldehyde gas and the solid phosphoric acid catalyst contact each other in a heterogenous system in the reaction vessel 4, a step of generating in the gas phase state as-is a reaction product gas including trioxane and unreacted formaldehyde gas is carried out.

When carrying out the above gas phase synthesis, the ratio of the mass per unit time of the formaldehyde gas supplied to the reaction vessel 4 to the mass of the solid phosphoric acid catalyst charged into the reaction vessel 4 (called the weight hourly space velocity WHSV [units: $h^{-1}$]) may be suitably adjusted in accordance with the trioxane yield, which varies with the form of the solid phosphoric acid catalyst used, the supported amount of acid, and the reaction conditions. The value of the WHSV (formaldehyde gas flow rate/catalyst mass) is preferably within the range of $1/50$ to $1$ $h^{-1}$. If the WHSV is less than $1/50$ $h^{-1}$, the catalyst mass with respect to the supplied formaldehyde becomes large, and there is the possibility that a conversion ratio of trioxane corresponding to only the added amount of the catalyst cannot be obtained, and there is the possibility that the cost of the catalyst will be high. On the other hand, if it exceeds $1$ $h^{-1}$, the amount of the supplied formaldehyde gas with respect to the catalyst becomes large, and therefore, sufficient contact time with the catalyst cannot be obtained and the reaction conversion rate to trioxane is reduced.

Further, as the other reaction conditions, concerning the temperature, taking into account that the present reaction is an exothermic equilibrium reaction, it is generally desired to be a low temperature, but the setting of a temperature which can avoid condensation and polymerization (generation of paraformaldehyde) of the formaldehyde gas before and after the reaction vessel 4 and inside the reaction vessel 4 is sought. Specifically, in the reaction vessel 4, it is preferable to provide a temperature measurement means which measures the temperature of the reaction product gas at the catalyst bed exit consisting of the solid phosphoric acid catalyst, and a control means which controls the temperature of a heating medium and/or the flow rate of the formaldehyde gas such that the temperature measured by the temperature measurement means is within the range of 80° C. to 120° C., and this control means preferably controls the temperature of the heating medium and/or the flow rate of the formaldehyde gas such that the temperature measured by the temperature measurement means is within the range of 90° C. to 110° C. If the reaction temperature becomes too low a temperature, a sufficient reaction rate cannot be obtained, and is not desirable in that the polymerization of the formaldehyde progresses and deposits on the catalyst bed. To the contrary, if the temperature exceeds 120° C., the gas phase equilibrium concentration of the trioxane is greatly reduced and side reactions are increased, which is not preferable. The reaction pressure is not particularly limited, but is preferably carried out in the range of atmospheric pressure to 5 MPa.

The type of the reaction vessel used as the reaction vessel 4 and the reaction form are not restricted, and it is possible to adopt batch-type, semibatch-type, and continuous flow type with a tank-shaped reaction vessel, or it is possible to adopt a fixed bed, fluidized bed, moving bed or the like flow type reaction vessel, but because the present reaction is an exothermic equilibrium reaction, a fixed bed flow type reaction vessel is preferably used, and it is desirable to efficiently remove heat from the catalyst bed. A fixed bed reaction vessel is a multitubular type tube reactor, and a heating medium flows on the outside. In order to increase the effect of the temperature control and heat removal by the heating medium, it is important that the inner diameter per one tube should not be too large, and it is normally a tube of no more than 100 mm, preferably no more than 50 mm. In a reaction vessel exceeding 100 mm, temperature gradients in the radial direction of the charged catalyst readily arise, and thermal storage readily occurs inside the filling which is disadvantageous to the reaction and is not preferable. Further, if the inner diameter of the reactor tube is too small, trouble in charging the molded body of the catalyst arises, therefore, it is preferable that the inner diameter is at least 10 mm or more.

Concerning the flow method of the formaldehyde gas to the reaction vessel 4, in the case that the reaction vessel 4 is a fixed bed or the like flow type reaction vessel, it may be either of upward flow•downward flow, but if it is an upward flow, in the case that the air column speed of the reaction product gas is increased, there is the danger of catalyst upwash and caution is required.

Further, in the present Examples, the type of gas used for the upward flow or downward flow is not particularly limited, and it may be carried out under an airflow flow of inert gas such as nitrogen argon or the like.

[Absorption Apparatus 5]

The absorption apparatus 5 absorbs trioxane from the reaction product gas produced in the reaction vessel 4 into a solvent. After the completion of the gas phase reaction, a reaction product gas including trioxane and unreacted formaldehyde gas is once drawn out while remaining in the gas phase without being condensed, in the reaction vessel. The present Examples are explained such that the trioxane gas included in the reaction product gas is absorbed into an organic solvent using an absorption column or the like, to obtain a trioxane solution, while the unreacted formaldehyde gas included in the reaction product gas is discharged to the outside of the absorption apparatus 5 while remaining in the gas phase, but it is not limited to this. For example, the trioxane component may be condensed by a condenser, or the trioxane may be solidified in a cooling column and the crystallized trioxane may be separated from the unreacted formaldehyde gas. After recovering the unreacted formaldehyde gas, it is possible to again circulate this gas to the reaction vessel 4, and to again carry out trioxane gas phase synthesis.

[Analysis Apparatus 6]

As the analysis apparatus 6, for example, gas chromatography (TCD-GC) using a thermal conductivity detector (TCD) can be mentioned. By using TCD-GC, it is possible to directly measure the yield and selectivity and the like of the formaldehyde and trioxane included in the reaction product gas.

Further, the formaldehyde analysis may be carried out by once collecting the reaction product gas as an aqueous solution, and titrating by the sodium sulfite process, and analysis of the trioxane and various secondary products may be carried out by measuring with gas chromatography (FID-GC) using a flame ionization detector (FID).

EXAMPLES

Below, the present invention is specifically explained showing Examples and Comparative Examples, but the present invention is not limited to these Examples.

Preparation of the Solid Phosphoric Acid Catalyst

TABLE 1

| | Example | | | | | | |
|---|---|---|---|---|---|---|---|
| | 1 | 2 | 3 | 4 | 5 | 6 | 7 |
| Carrier | Spherical aluminum hydrosilicate | Spherical aluminum hydrosilicate | Spherical aluminum hydrosilicate | Diatomaceous earth I | Diatomaceous earth II | Diatomaceous earth II | Spherical aluminum hydrosilicate + diatomaceous earth II |
| Phosphoric acid | Orthophosphoric acid | Orthophosphoric acid | Orthophosphoric acid | Orthophosphoric acid | Orthophosphoric acid | Orthophosphoric acid | Orthophosphoric acid |
| Conditions of spraying etc. | 80° C., vacuum spraying + impregnation | 80° C., vacuum spraying + impregnation | 80° C., vacuum spraying + impregnation | mixing | mixing | mixing | mixing |
| Conditions of sintering etc. | 220° C. | 320° C. | 500° C. | 320° C. | 320° C. | 500° C. | 320° C. |

TABLE 2

| | Comparative Example | | | | | |
|---|---|---|---|---|---|---|
| | 1 | 2 | 3 | 4 | 5 | 6 |
| Carrier | Spherical aluminum hydrosilicate | Spherical aluminum hydrosilicate | silica gel | Commercial product I | Commercial product II | Commercial product III |
| Phosphoric acid | Orthophosphoric acid | Orthophosphoric acid | Orthophosphoric acid | | | |
| Conditions of spraying etc. | 80° C., vacuum spraying + impregnation | 80° C., vacuum spraying + impregnation | 80° C., vacuum spraying + impregnation | | | |
| Conditions of sintering etc. | 80° C. drying | 80° C. drying | 80° C. drying | | | |

Example 1

After spraying a quantity of a phosphoric acid solution (orthophosphoric acid 75% aqueous solution; made by Wako Pure Chemical Industries, Ltd., reagent special grade) onto spherical aluminum hydrosilicate (made by Clariant Catalysts K.K.) with an average particle diameter of 5.4 mm at 80° C. under vacuum conditions such that 55 parts by mass of the carrier were impregnated with 45 parts by mass of the phosphoric acid, by sintering at 220° C. in air, the solid phosphoric acid catalyst of Example 1 was obtained.

Example 2

After impregnating by spraying a prescribed amount of a phosphoric acid aqueous solution at 80° C. under vacuum conditions onto the above spherical aluminum hydrosilicate, by sintering at 320° C. in air, the solid phosphoric acid catalyst of Example 2 was obtained.

Example 3

After impregnating by spraying a prescribed amount of the above phosphoric acid aqueous solution at 80° C. under vacuum conditions onto the above spherical aluminum hydrosilicate, by sintering at 500° C. in air, the solid phosphoric acid catalyst of Example 3 was obtained.

Example 4

Diatomaceous earth I (diatomaceous earth produced in the U.S.) was mixed with a prescribed amount of the above phosphoric acid aqueous solution, and molded into pellet form with a diameter of about 4.5 mm. After this, the molded body was sintered at 320° C. in air, to obtain the solid phosphoric acid catalyst of Example 4.

Example 5

Diatomaceous earth II (diatomaceous earth produced in India) was mixed with a prescribed amount of the above phosphoric acid aqueous solution, and molded into pellet form with a diameter of about 4.5 mm. After this, the molded body was sintered at 320° C. in air, to obtain the solid phosphoric acid catalyst of Example 5.

Example 6

The solid phosphoric acid catalyst of Example 6 was obtained by the same method as Example 5, except that the sintering temperature was 500° C.

Example 7

After mixing a powered aluminum hydrosilicate (made by Clariant Catalysts K.K.) and the above diatomaceous earth II in a mass ratio of 2:1, this was mixed with a prescribed amount of the above phosphoric acid aqueous solution and pellets with a diameter of about 4.5 mm were formed. After this, the molded body was sintered at 320° C. in air, to obtain the solid phosphoric acid catalyst of Example 7.

Comparative Example 1

After spraying and impregnating a prescribed amount of a phosphoric acid aqueous solution onto the above spherical aluminum hydrosilicate at 80° C. under vacuum conditions, by further vacuum drying at 80° C. for 1 hr the solid phosphoric acid catalyst according to Comparative Example 1 was obtained.

Comparative Example 2

The solid phosphoric acid catalyst of Comparative Example 2 was obtained by the same method as Comparative Example 1 except that the above spherical aluminum hydrosilicate was a powdered aluminum hydrosilicate.

Comparative Example 3

After a high purity silica gel (product name: CARiACT Q 10, made by Fuji Silysia Chemical Ltd.) was sprayed and impregnated with a predetermined amount of the above phosphoric acid aqueous solution at 80° C. under vacuum conditions, by further vacuum drying at 80° C. for 1 hr the solid phosphoric acid catalyst according to Comparative Example 3 was obtained.

Comparative Example 4

The solid phosphoric acid catalyst of Comparative Example 4 was the commercial product I (product name: C84-5, silicon phosphate catalyst, made by former Sud-chemie Catalyst Co. (currently Clariant Catalysts K.K.)).

Comparative Example 5

The solid phosphoric acid catalyst of Comparative Example 5 was the commercial product II (product name: T-8703, solid phosphoric acid catalyst having aluminum phosphate as the main component, made by Clariant Catalysts K.K.).

Comparative Example 6

The solid phosphoric acid catalyst of Comparative Example 6 was the commercial product III (product name: Nafion (registered trademark) NR-50, obtained as a reagent from Sigma-Aldrich Corporation).

[Evaluation of the Acid Quantity]

The acid quantity was evaluated for the solid phosphoric acid catalysts of the Examples and Comparative Examples. The evaluation of the acid quantity was carried out using a BelCAT (made by BEL Japan, Inc.) $NH_3$-TPD measurement apparatus. The results are shown in Table 3 and Table 4.

[Evaluation of the Surface Area]

The average specific surface area was evaluated for the solid phosphoric acid catalysts of the Examples and Comparative Examples. The evaluation of the average specific surface area was measured by a BET absorption process using a Macsorb automatic surface area analyzer (made by Mountech Co., Ltd.). The results are shown in Table 3 and Table 4.

[Structural Analysis of the Catalyst Composition]

Structural analysis of the catalyst components relating to the silicon phosphate oxide (below SPO) was carried out for the solid phosphoric acid catalysts of the Examples and Comparative Examples. This analysis was carried out using an X'Pert PRO X-ray diffraction apparatus (made by Rikadenki K.K.). The results are shown in Table 3 and Table 4.

TABLE 3

| | | | Example | | | | | | |
|---|---|---|---|---|---|---|---|---|---|
| | | | 1 | 2 | 3 | 4 | 5 | 6 | 7 |
| Catalyst characteristics | Acid quantity (NH$_3$-TPD) | mmol/g | 0.87 | 0.22 | 0.09 | 0.19 | 0.24 | 0.16 | 0.12 |
| | Surface area of catalyst | m$^2$/g | 14.7 | 5.5 | 2.9 | 1.5 | 2.7 | 1.7 | 2.8 |
| | Detection of SPO by XRD (Present/absent) | | SPO Present | SPO Present | SPO Present | SPO Present | SPO Present | SPO Present | SPO Present |

TABLE 4

| | | | Comparative Example | | | | | |
|---|---|---|---|---|---|---|---|---|
| | | | 1 | 2 | 3 | 4 | 5 | 6 |
| Catalyst characteristics | Acid quantity (NH$_3$-TPD) | mmol/g | 3.2 | 9.2 | 5.6 | 6.4 | 0.6 | 0.5 |
| | Surface area of catalyst | m$^2$/g | 19.0 | 16.8 | 81.2 | 1.1 | 51.9 | — |
| | Detection of SPO by XRD (Present/absent) | | SPO Absent | SPO Absent | SPO Absent | SPO Present | SPO Absent (Aluminum phosphate) | SPO Absent |

A silicon phosphate oxide is produced at a solid phosphoric acid catalyst obtained by sintering the carrier material to which the phosphoric acid is attached at no less than 200° C. Further, the acid quantity obtained by the NH$_3$-TPD measurement method was confirmed to be no more than 5 mmol per 1 g of the solid phosphoric acid catalyst (Examples 1 to 7).

On the other hand, a solid phosphoric acid catalyst obtained by drying at a temperature of less than 200° C. was confirmed to not include a silicon phosphate oxide (Comparative Examples 1 to 3). Further, also in the commercial products, it was confirmed that the total quantity of the acid exceeded 5 mmol per 1 g of the solid phosphoric acid catalyst (Comparative Example 4), or did not include a silicon phosphate oxide (Comparative Examples 5 and 6).

[Trioxane Gas Phase Synthesis I—Gas Phase Synthesis of Trioxane with a Mixed Gas of Formaldehyde Gas/Nitrogen Gas as the Raw Material]

A formaldehyde aqueous solution including 50 mass % formaldehyde, and 2,4-dimethyl-1,5-pentanediol (product name: PD-9, made by Kyowa Hakko Chemical Co., Ltd.) were mixed such that the mole ratio of the hydroxyl groups included in the alcohol with respect to the formaldehyde included in the formaldehyde aqueous solution (mole number of the hydroxyl groups included in the alcohol/mole number of the formaldehyde included in the formaldehyde aqueous solution) was 1.3, and this was reacted for 12 hr under room temperature and the hemiformal conversion was carried out. The hemiformal aqueous solution produced by this reaction was continuously supplied to a low pressure dehydration column at a rate of 1000 g/hr, and dehydration was carried out under conditions of 75° C. and 35 mmHg, and a hemiformal concentrate was obtained.

Then, 120 ml of the above hemiformal concentrate was introduced into a flask, and further a roller pump was provided to carry out continuous supply•removal of the hemiformal at a fixed rate of 1 ml/min from the outside of the flask. Further, at the same time, a nitrogen gas was supplied into the flask at a fixed flow rate (50 to 100 ml/min). This flask was immersed in an oil bath at 160 to 170° C. and a pyrolysis reaction of the hemiformal concentrate was carried out, and a mixed gas of formaldehyde gas and nitrogen was prepared. Here, the nitrogen flow rate was suitably adjusted such that the mixing ratio of the formaldehyde gas and nitrogen gas was a mol ratio between 60:40 and 75:25.

Then, the solid phosphoric acid catalysts of Examples 1 to 7 and Comparative Examples 1 to 6 were introduced into a reaction tube of 18 mm (inner diameter)×200 mm (length), and the catalyst bed inside the reaction tube was heated from outside of the reaction tube by an electric heater. The mixed gas of formaldehyde and nitrogen obtained by the pyrolysis of the hemiformal was continuously supplied by a downward flow into the fixed bed reaction vessel charged with the catalyst, whereby a gas phase synthesis of trioxane was implemented. The reaction temperature in the catalyst bed was set to 100° C. by the setting of the electric heater, but the actual internal temperature of the catalyst bed was increased by the generated heat. The exact temperature was detected by a thermocouple, and in particular, the reaction product gas temperature at the exit portion of the catalyst bed was recorded. The results are shown in Table 5 and Table 6.

On the other hand, the reaction product gas was collected in 100 ml of water and while exchanging the water every hour, sampling was carried out, and the reaction was continued for a total of no less than 6 hours. The analysis of the reaction product gas was implemented by formaldehyde analysis of the collected aqueous solution (titration by sodium sulfite) and analysis of trioxane and various secondary products (FID-GC). The results are shown in Table 5 and Table 6.

TABLE 5

| | | | Example | | | | | | |
|---|---|---|---|---|---|---|---|---|---|
| | | | 1 | 2 | 3 | 4 | 5 | 6 | 7 |
| Trioxane synthesis I | Reaction gas flow rate HCHO Feed quantity | g/h | 5.5 | 5.3 | 4.6 | 5.2 | 5.0 | 4.6 | 5.2 |
| | Reaction gas temperature (catalyst exit) | °C. | 107 | 107 | 106 | 106 | 106 | 106 | 106 |
| | Yield and selectivity of reaction product | | | | | | | | |
| | Trioxane yield | wt % | 32.3 | 33.2 | 41.3 | 35.4 | 31.6 | 31.5 | 31.6 |
| | Side reactions other than trioxane | wt % | 0.6 | 0.5 | 1.3 | 0.8 | 0.6 | 0.5 | 0.8 |
| | Trioxane selectivity | % | 98.1 | 98.4 | 96.9 | 97.8 | 98.2 | 98.3 | 97.5 |

TABLE 6

| | | | Comparative Example | | | | | |
|---|---|---|---|---|---|---|---|---|
| | | | 1 | 2 | 3 | 4 | 5 | 6 |
| Trioxane synthesis I | Reaction gas flow rate HCHO Feed quantity | g/h | 5.0 | 5.2 | 4.9 | 5.3 | 3.9 | 2.9 |
| | Reaction gas temperature (catalyst exit) | °C. | 100 | 111 | 102 | 106 | 102 | 110 |
| | Yield and selectivity of reaction product | | | | | | | |
| | Trioxane yield | wt % | 33.5 | 23.2 | 21.6 | 30.2 | 4.9 | 13.5 |
| | Side reactions other then trioxane | wt % | 3.9 | 1.7 | 1.0 | 2.4 | 0.2 | 1.2 |
| | Trioxane selectivity | % | 89.6 | 93.1 | 95.7 | 92.7 | 96.1 | 91.6 |

The catalyst obtained by sintering the carrier material with the attached phosphoric acid component included a silicon phosphate oxide. Further, the acid quantity obtained by the $NH_3$-TPD measurement method was no more than 5 mmol per 1 g of the solid phosphoric acid catalyst. It was confirmed that by using such a solid phosphoric acid catalyst, it is possible to obtain trioxane with a high yield and a high selectivity (Examples 1 to 7).

On the other hand, for a solid phosphoric acid catalyst prepared only by drying for 1 hour at 80° C., only the carrier component was observed by X-ray diffraction, and no form of presence of a silicon phosphate oxide could be confirmed (Comparative Examples 1 to 3). The form of presence of the phosphorous in Comparative Examples 1 to 3 is conjectured to be phosphoric acid at the catalyst surface or phosphoric acid molecules weakly interacting with the carrier. The solid phosphoric acid catalysts according to Comparative Examples 1 to 3, besides having the common characteristic that the SPO was not detected, have the various characteristics such that the acid quantity was large and no less than 5 mmol/g, the specific surface area by the BET method was no less than 20 m$^2$/g, and even when trioxane gas phase synthesis was carried out using these catalysts, it was confirmed that it was not possible to obtain yields or selectivities as high as in the Examples.

Further, even if phosphorous is partially present in the form of a silicon phosphate oxide, for a solid phosphoric acid catalyst where the acid quantity is large and no less than 5 mmol/g, it was confirmed that it was not possible to obtain a yield or selectivity as high as in the Examples (Comparative Example 4).

Further, also in a solid phosphoric acid catalyst where the main component is aluminum phosphate, it was established that it was not possible to obtain a yield or selectivity as high as in the Examples (Comparative Example 5).

Further, also in a solid phosphoric acid catalyst where the acid is a sulfonic acid form, it was established that it was not possible to obtain a yield or selectivity as high as in the Examples (Comparative Example 6).

[Trioxane Gas Phase Synthesis II—Gas Phase Synthesis of Trioxane with a Mixed Gas of Formaldehyde Gas/Nitrogen Gas/Benzene as the Raw Material]

A reaction was assumed of a three component system including benzene as an organic compound component in addition to formaldehyde and nitrogen gas, as the mixed gas components when carrying out a gas phase trimerization reaction, and the case of adding benzene in advance to a hemiformal solution and carrying out pyrolysis was also studied. The added amount of benzene was adjusted so that the benzene is about 15 to 25 parts by mass with respect to the formaldehyde at the time of the gas phase trimerization reaction. In this gas phase synthesis, the solid phosphoric acid catalysts of Examples 1 to 7 and Comparative Examples 1 to 6, and for the solid phosphoric acid catalysts, the influence on the trioxane yield•selectivity and hue changes (ΔE value) of the catalyst after the gas phase synthesis of trioxane, were evaluated. The results are shown in Table 7 and Table 8. Further, the ΔE value is a value obtained from the following formula by the ΔL, Δa, and Δb measured by an SE-2000 color difference meter (made by Nippon Denshoku Industries Co., Ltd.).

$$\Delta E = \sqrt{\Delta L^2 + \Delta a^2 + \Delta b^2}$$

TABLE 7

| | | | Example | | | | | | |
|---|---|---|---|---|---|---|---|---|---|
| | | | 1 | 2 | 3 | 4 | 5 | 6 | 7 |
| Trioxane synthesis II | Reaction gas flow rate HCHO FEED QUANTITY | g/h | 5.7 | 5.6 | 5.7 | 5.2 | 4.8 | 5.4 | 5.2 |
| | Bzfeed quantity | g/h | 1.1 | 1.1 | 1.1 | 1.1 | 1.1 | 1.1 | 1.1 |
| | Reaction gas temperature (catalyst exit) | °C. | 108 | 109 | 104 | 105 | 106 | 108 | 111 |
| | Yield and selectivity of reaction product | | | | | | | | |
| | Trioxane yield | wt % | 30.4 | 25.3 | 32.3 | 29.6 | 30.5 | 33.0 | 25.1 |
| | Side reactions other than trioxane | wt % | 0.8 | 0.7 | 0.6 | 0.6 | 0.5 | 0.6 | 0.7 |
| | Trioxane selectivity | % | 97.5 | 97.4 | 97.0 | 98.1 | 98.3 | 98.2 | 97.4 |
| | Hue change of catalyst after reaction | ΔE | 22.1 | 21.5 | 12.3 | 5.1 | 7.6 | 4.7 | 9.1 |

TABLE 8

| | | | Comparative Example | | | | | |
|---|---|---|---|---|---|---|---|---|
| | | | 1 | 2 | 3 | 4 | 5 | 6 |
| Trioxane synthesis II | Reaction gas flow rate HCHO FEED QUANTITY | g/h | 5.0 | 5.5 | 5.8 | 4.8 | 5.1 | 5.1 |
| | Bzfeed quantity | g/h | 1.0 | 1.0 | 1.6 | 0.9 | 1.1 | 1.6 |
| | Reaction gas temperature (catalyst exit) | °C. | 113 | 117 | 115 | 110 | 102 | 125 |
| | Yield and selectivity of reaction product | | | | | | | |
| | Trioxane yield | wt % | 16.2 | 12.1 | 22.7 | 11.3 | 3.5 | 5.9 |
| | Side reactions other than trioxane | wt % | 1.1 | 1.1 | 0.8 | 1.0 | 0.4 | 0.8 |
| | Trioxane selectivity | % | 93.4 | 91.6 | 96.7 | 92.2 | 89.7 | 88.0 |
| | Hue change of catalyst after reaction | ΔE | 35.9 | 48.6 | 59.0 | 54.0 | 5.8 | 37.3 |

Usually, under the presence of an organic compound such as benzene or the like, the deposition of carbides (coking) on a catalyst surface is promoted, and there is a tendency for the catalyst itself to be observed to become notably reduced in activity and discolored (blackened), but upon using the solid phosphoric acid catalyst according to the Examples, it was confirmed that a notable deposition of carbon substances does not occur on the surface of the catalyst, and the ΔE value which is an index showing hue change due to discoloration was also generally small (Examples 1 to 7). Further, it was also confirmed that in the three component system of formaldehyde gas/nitrogen gas/benzene, there is some decrease in trioxane absorption accompanying a reduction of the partial pressure of the formaldehyde gas due to the benzene, but almost no decrease in the selectivity could be observed.

On the other hand, in the case of using the solid phosphoric acid catalysts prepared by only drying for 1 hr at 80° C., it was confirmed that in the three component system of formaldehyde gas/nitrogen gas/benzene, coking readily occurred at the catalyst itself at when performing the gas phase trimerization reaction, the ΔE value was a high value of no less than 30, and blackening due to carbonization was notable (Comparative Examples 1 to 3).

Further, in the case of using an solid phosphoric acid catalyst where the acid quantity is large and no less than 5 mmol/g, even if phosphorous was partially present in the form of a silicon phosphate oxide, it was confirmed that in the three component system of formaldehyde gas/nitrogen gas/benzene, coking readily occurred at the catalyst itself when performing the gas phase trimerization reaction, and blackening due to carbonization was notable (Comparative Example 4).

Further, in the case of an aluminum phosphate type catalyst not having an SPO, it was confirmed that in the three component system of formaldehyde gas/nitrogen gas/benzene, blackening due to carbonization was relatively mild, but the yield of trioxane was extremely low (Comparative Example 5).

Further, in the case of using a solid acid catalyst having a Teflon (registered trademark) type skeleton having sulfonic acid residues, the acid is a component deriving from the sulfonic acid residue, but it was confirmed that the trioxane yield is low, and also in the three component system of formaldehyde gas/nitrogen gas/benzene, coking readily occurred at the catalyst itself at when performing the gas phase trimerization reaction, and blackening due to carbonization was notable (Comparative Example 6).

EXPLANATION OF REFERENCE NUMERALS

1. trioxane preparation apparatus
2. hemiformal generation apparatus
3. hemiformal pyrolysis vessel 4. reaction vessel
5. absorption apparatus
6. analysis apparatus

The invention claimed is:

1. A solid phosphoric acid catalyst comprising a silicon phosphate oxide, wherein a quantity of acid determined by an $NH_3$-TPD measurement method is no more than 5 mmol per 1 g of catalyst mass.

2. The solid phosphoric acid catalyst according to claim 1, wherein a specific surface area according to a BET method is no more than 20 $m^2/g$.

3. The solid phosphoric acid catalyst according to claim 1, further comprising one or more carriers selected from the group consisting of porous silica, aluminum hydrosilicate and diatomaceous earth.

4. The solid phosphoric acid catalyst according to claim 3, wherein the silicon phosphate oxide is a dehydrated composite compound of the carrier, and one or more phosphoric acids selected from the group consisting of orthophosphoric acid, pyrophosphoric acid, polyphosphoric acid, and a precursor thereof.

5. The solid phosphoric acid catalyst according to claim 1, wherein the catalyst is obtained by sintering a carrier material to which a phosphoric acid component is attached at no less than 200° C.

6. A method for producing trioxane, wherein the solid phosphoric acid catalyst according to claim 1 is charged into a reaction vessel, and formaldehyde gas and the solid phosphoric acid catalyst are contacted in a heterogeneous system, whereby trioxane remaining in a gas phase state is continuously extracted from the reaction vessel.

7. The method for producing trioxane according to claim 6, wherein the reaction vessel is a cylindrically shaped fixed bed reaction vessel with an inner diameter of no more than 100 mm, and the solid phosphoric acid catalyst having an average particle diameter of no more than 10 mm is charged in the fixed bed reaction vessel.

8. The method for producing trioxane according to claim 6, wherein, in the reaction vessel in which the solid phosphoric acid catalyst is charged, a temperature measurement means which measures a temperature of a reaction product gas at a catalyst bed exit, and a control means which controls a temperature of a heating medium and/or a flow rate of the formaldehyde gas such that a measured temperature by the temperature measurement means is in a range of 80° C. to 120° C., are provided.

* * * * *